United States Patent
Jacovella

(10) Patent No.: US 10,463,643 B2
(45) Date of Patent: Nov. 5, 2019

(54) COMPOSITION COMPRISING A COMPOUND FROM THE FAMILY OF AVERMECTINS AND DOXYCYCLINE FOR THE TREATMENT OF ROSACEA

(71) Applicant: GALDERMA SA, Cham (CH)

(72) Inventor: Jean Jacovella, Antibes (FR)

(73) Assignee: GALDERMA SA, Cham (CH)

( * ) Notice: Subject to any disclaimer, the term of this patent is extended or adjusted under 35 U.S.C. 154(b) by 0 days.

(21) Appl. No.: 15/512,486

(22) PCT Filed: Sep. 18, 2015

(86) PCT No.: PCT/EP2015/071402
§ 371 (c)(1),
(2) Date: Mar. 17, 2017

(87) PCT Pub. No.: WO2016/042117
PCT Pub. Date: Mar. 24, 2016

(65) Prior Publication Data
US 2017/0273931 A1    Sep. 28, 2017

(30) Foreign Application Priority Data
Sep. 18, 2014   (FR) .................................... 14 58799

(51) Int. Cl.
*A61K 31/33*    (2006.01)
*A61K 31/65*    (2006.01)
*A61K 31/7048*  (2006.01)
*A61K 9/00*     (2006.01)

(52) U.S. Cl.
CPC ............ *A61K 31/33* (2013.01); *A61K 9/0014* (2013.01); *A61K 9/0053* (2013.01); *A61K 31/65* (2013.01); *A61K 31/7048* (2013.01)

(58) Field of Classification Search
CPC .. A61K 31/65; A61K 31/7048; A61K 9/0014; A61K 9/0053
See application file for complete search history.

(56) References Cited

U.S. PATENT DOCUMENTS 5,952,372 A    9/1999   McDaniel

FOREIGN PATENT DOCUMENTS

| EP | 2368557 A1 | 9/2011 |
| WO | 2004/093886 A1 | 11/2004 |
| WO | 2014/049295 A1 | 4/2014 |

OTHER PUBLICATIONS

Lacey et al., "Mite-related bacterial antigens stimulate inflammatory cells in rosacea". British Journal of Dermatology, vol. 157(3), 474-481 (Year: 2007).*
Korting et al., "Tetracycline actions relevant to rosacea treatment". Skin Pharmacol. Physiol., vol. 22, 287-294 (Year: 2009).*
International Search Report and Written Opinion of the International Searching Authority dated Feb. 5, 2016 corresponding to International Patent Application No. PCT/EP2015/071402, 10 pages.

* cited by examiner

*Primary Examiner* — Barbara P Badio
(74) *Attorney, Agent, or Firm* — Foley & Lardner LLP; Sunit Talapatra

(57) ABSTRACT

The use of a composition comprising a compound from the family of avermectins, preferably ivermectin, and doxycycline or one of the salts thereof that is pharmaceutically acceptable in the treatment and/or slowing of the appearance of the symptoms of rosacea is described.

19 Claims, No Drawings

COMPOSITION COMPRISING A COMPOUND FROM THE FAMILY OF AVERMECTINS AND DOXYCYCLINE FOR THE TREATMENT OF ROSACEA

CROSS-REFERENCE TO PRIOR APPLICATIONS

This application is a National Stage of PCT/EP2015/071402, filed Sep. 18, 2015, and designating the United States (published on Mar. 24, 2016, as WO 2016/042117 A1), which claims priority under 35 U.S.C. § 119 to French Application No. 1458799, filed Sep. 18, 2014, each hereby expressly incorporated by reference in its entirety and each assigned to the assignee hereof.

The present invention relates to compositions used in the treatment and/or the delaying of the onset of the symptoms of rosacea.

TECHNOLOGICAL BACKGROUND OF THE INVENTION

Rosacea is a common chronic inflammatory dermatosis characterized according to form by the presence of erythema, telangiectasias, edema, papules, pustules, ocular lesions and occasionally rhinophyma. It is most often bilateral and it affects predominantly the median portion of the face, the forehead, the nose, the chin and the cheeks.

Rosacea generally develops in adults aged 30 to 50 years and is much more common among people with fair skin. It affects women more particularly, although this affection is generally more severe in men. Rosacea is chronic and persists for years with periods of exacerbation and remission.

The pathogenesis of rosacea is poorly understood. Many factors may be involved, such as, for example, psychological factors, environmental factors (sun exposure, temperature, humidity), emotional factors (stress), food-related factors (alcohol, spices), hormonal, gastrointestinal and vascular disorders, even infection by *Helicobacter pylori* and the characteristic presence of the parasite *Demodex folliculorum* or *Demodex brevis* among rosacea patients.

Rosacea can be Classified as Follows:
- Type I: Erythematotelangiectatic rosacea, mainly characterized by persistent central facial erythema and episodic reddening or flushing. Often, this type is also characterized by edema, roughness or scaling and the appearance of dilated blood vessels (telangiectasia) as well as by burning and stinging sensations.
- Type II: Papulopustular rosacea, characterized by persistent central facial erythema and by the appearance of transient central facial papules or pustules. These symptoms are sometimes accompanied by burning and stinging sensations. This type may follow or occur in combination with type I.
- Type III: Phymatous rosacea, marked by thickening skin and the appearance of irregular nodules. Although the nose is often the most affected area, becoming very large and swollen ("rhinophyma"), other locations are also observed: the chin, the forehead, the cheeks and the ears. This type can follow or occur in combination with type I and II.
- Type IV: Ocular rosacea, characterized by red, irritated eyes which may be watery and bloodshot. Symptoms may include the sensation of having a foreign body in the eye, excessive watering, light sensitivity, blurred vision, a sensation of burning, dryness or stinging, itching and alacrima.

Classically, rosacea can be treated orally or topically with antibiotics such as tetracyclines, erythromycin, clindamycin, but also with vitamin A, salicylic acid, antifungal agents, steroids, metronidazole or with isotretinoin for severe forms or with azelaic acid. However, the use of these antibiotics does not make it possible to effectively treat and/or prevent all the symptoms associated with rosacea and can often cause side effects and intolerance problems in many patients.

Rosacea can also be treated topically using ivermectin to target the parasite *Demodex folliculorum* or *Demodex brevis* as proposed in the patent U.S. Pat. No. 5,952,372. However, the effects of resistance of this parasite to ivermectin may occur, thus decreasing the efficacy of such a treatment or making it ineffective.

Thus, it must be acknowledged that there exists a need to provide a more effective rosacea treatment that does not cause side effects and intolerance problems for the patient. In particular, there is to date no rosacea treatment that can replace those that have become less effective or ineffective due to resistance phenomena.

SUMMARY OF THE INVENTION

It is to the credit of the Applicant to have discovered that a combination of a compound of the avermectin family, particularly ivermectin, with doxycycline provides a more effective treatment of rosacea with fewer side effects, in particular when a resistance of *Demodex* develops, particularly a resistance of *Demodex* to ivermectin.

In particular, such a combination makes it possible to substantially reduce the duration of the treatment and to obtain a greater reduction of the symptoms of rosacea. Furthermore, the combination of these two active agents makes it possible to obtain a certain advantage in terms of efficacy and tolerance, thus making it possible either to increase the therapeutic effect for similar doses, or to retain the same therapeutic effect while decreasing the doses. Lastly, such a combination makes it possible to guarantee the efficacy of the treatment during the appearance of a resistance of *Demodex* to avermectins or to postpone or delay the onset of this resistance.

The object of the present invention is thus to propose a composition comprising a compound of the avermectin family and doxycycline or a pharmaceutically acceptable salt thereof, for use in the treatment and/or the delaying of the onset of the symptoms of rosacea.

The object of the present invention is also to propose a composition comprising a compound of the avermectin family and doxycycline or a pharmaceutically acceptable salt thereof, for use in reducing, inhibiting or slowing the onset of the symptoms associated with rosacea, in particular erythema, papules, pustules, telangiectasia.

Advantageously, the compound of the avermectin family is ivermectin. Preferably, the rosacea is subtype I, II and IV, and more preferentially subtype II. In another preferred embodiment, the compositions of the invention are used in the treatment and/or the delaying of the onset of the symptoms of a rosacea associated with/exhibiting a resistance of *Demodex* to avermectins, preferentially to ivermectin.

In a particular embodiment, the compound of the avermectin family present in the compositions of the invention represents between 0.001 and 10%, preferentially between 0.001 and 5%, and more preferentially between 0.1 and 2% by weight, in relation to the total weight of the composition.

Advantageously, the compound of the avermectin family represents between 0.5 and 1%, preferably 0.5% or 1%, and more preferentially 1% by weight, in relation to the total weight of the composition.

In another particular embodiment, the doxycycline or a pharmaceutically acceptable salt thereof present in the compositions of the invention represents between 0.0001 and 5%, preferably between 0.001 and 3% by weight, in relation to the total weight of the composition.

Particularly, the compositions used in the invention are intended to be administered topically or orally.

According to a particular embodiment, the compositions of the invention are intended to be administered to a patient at an effective therapeutic dose of a compound of the avermectin family of between 100 µg and 5 g, between 100 µg and 3 g, between 100 µg and 1 g, preferably between 150 µg and 500 mg, and more preferentially between 200 µg and 200 mg per day.

According to another particular embodiment, the compositions of the invention are intended to be administered to a patient at an effective therapeutic dose of doxycycline or a pharmaceutically acceptable salt thereof of between 100 µg and 1 g, preferably between 100 µg and 500 mg, more preferentially between 10 and 300 mg per day, and still more preferably at an effective therapeutic dose of 40, 100 or 200 mg per day.

Another object of the invention relates to a kit comprising (a) a composition comprising a compound of the avermectin family, preferentially ivermectin and (b) a composition comprising doxycycline or a pharmaceutically acceptable salt thereof, as a combination product for simultaneous, separate or sequential use in the treatment and/or the delaying of the onset of the symptoms of rosacea.

Preferably, the rosacea is subtype I, II and IV, and more preferentially subtype II.

In another preferred embodiment, the kits according to the invention are used in the treatment and/or the delaying of the onset of the symptoms of a rosacea associated with/exhibiting a resistance of *Demodex* to avermectins, preferentially to ivermectin.

In a particular embodiment, the composition of the kit comprising a compound of the avermectin family, preferentially ivermectin, is intended to be administered at an effective therapeutic dose of between 100 µg and 5 g, between 100 µg and 3 g, between 100 µg and 1 g, preferably between 150 µg and 500 mg, and more preferentially between 200 µg and 200 mg per day, and the composition of the kit comprising doxycycline or a pharmaceutically acceptable salt thereof is intended to be administered at an effective therapeutic dose of between 100 µg and 1 g, preferably between 100 µg and 500 mg, more preferentially between 10 and 300 mg per day, and still more preferably at an effective therapeutic dose of 40, 100 or 200 mg per day.

DETAILED DESCRIPTION OF THE INVENTION

The inventors identified a novel use of a composition in the treatment and/or the delaying of the onset of the symptoms of rosacea and discovered, surprisingly, that the combination of the two active agents, namely a compound of the avermectin family, particularly ivermectin, and doxycycline, made it possible to treat and/or delay the onset of the symptoms of rosacea. In particular, it was shown that such a combination was effective for treating the various types of a rosacea including when phenomena of resistance of *Demodex* were observed.

The invention thus relates to a composition comprising a compound of the avermectin family, preferentially ivermectin, and doxycycline or a pharmaceutically acceptable salt thereof, for use in the treatment and/or the delaying of the onset of the symptoms of rosacea, preferentially subtype I, II and IV rosacea as defined above, and more preferentially subtype II rosacea.

The invention also relates to a combination of a compound of the avermectin family, preferentially ivermectin, and doxycycline or a pharmaceutically acceptable salt thereof, for use in the treatment and/or the delaying of the onset of the symptoms of rosacea.

The invention also relates to methods or processes employing a composition comprising a compound of the avermectin family, preferentially ivermectin, and doxycycline or a pharmaceutically acceptable salt thereof as defined in the present application for administration in an effective therapeutic quantity to a patient suffering from rosacea.

The invention also relates to a method for treating and/or slowing the onset of the symptoms of rosacea comprising the administration of a therapeutically effective quantity of a compound of the avermectin family, preferentially ivermectin, and doxycycline or a pharmaceutically acceptable salt thereof, to a patient suffering from rosacea. Preferably, the method comprises the administration of a composition as defined in the present application comprising the compound of the avermectin family and doxycycline or a pharmaceutically acceptable salt thereof in a therapeutically effective quantity.

The invention also relates to the use of a composition as defined in the present application comprising a compound of the avermectin family and doxycycline or a pharmaceutically acceptable salt thereof for the preparation of a medicinal product for treating and/or delaying the onset of the symptoms of rosacea.

Active Agents

The avermectin class is a group of macrocyclic lactones produced by the bacterium *Streptomyces avermitilis* (Reynolds JEF (Ed) (1993) Martindale. The extra pharmacopoeia. 29th Edition. Pharmaceutical Press, London). Among these macrocyclic lactones belonging to the avermectin class, mention may be made of ivermectin, avermectin, abamectin, doramectin, eprinomectin, selamectin, aversectin B, AB or C, emamectin B1b and derivatives thereof, or latidectin. According to the invention, the compound of the avermectin family is preferentially ivermectin.

Ivermectin is a mixture of 22,23-dihydroavermectin $B_{1a}$ and 22,23-dihydroavermectin $B_{1b}$. Ivermectin contains mostly 22,23-dihydroavermectin $B_{1a}$.

Ivermectin is known in the prior art for its antiparasitic and anthelmintic properties. In the mid—1980s, the molecule was presented as a broad-spectrum antiparasitic drug for veterinary use (Campbell, W. C., et al., (1983). Ivermectin: a potent new antiparasitic agent. Science, 221, 823-828). It is effective against most common intestinal worms (except tapeworms), most Acari, and a few lice. It has a high affinity for glutamate-gated chloride channels, in particular those gated by the neurotransmitter GABA (gamma-aminobutyric acid), present in the nerve and muscle cells of invertebrates, conferring an antiparasitic activity thereon. More particularly, its binding on these channels promotes an increase in membrane permeability to chloride ions, leading to hyperpolarization of the nerve or muscle cell. The result is neuromuscular paralysis that can lead to the death of certain parasites. Ivermectin also interacts with other chloride channels.

Ivermectin is used traditionally in the dermatological treatment of endoparasitic manifestations such as onchocerciasis and myiasis. The patents U.S. Pat. No. 6,133,310 and U.S. Pat. No. 5,952,372 also disclose the use of ivermectin in the treatment of rosacea in order to reduce and eliminate the parasite *Demodex folliculorum* present on the patient's skin. However, resistance phenomena are possible, making such treatments more or less ineffective in the treatment of rosacea associated with/exhibiting a resistance of *Demodex* to ivermectin.

Doxycycline is a cycline molecule known in the prior art for its antibiotic properties. It refers to alpha-6-deoxy-5-oxytetracycline or 1,4,4a,5,5a,6,11,12a-octahydro-3,5,10,12,12a-pentahydroxy-6-methyl-1,11-dioxo-2-naphthacene-carboxamide of formula:

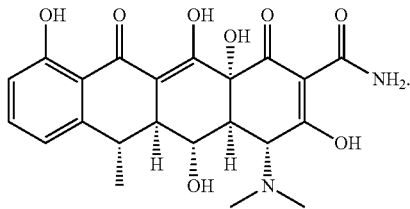 [SMILES: C[C@@H]1c2cccc(O)c2C(=O)C2=C(O)[C@@]3(O)C(=O)C(C(N)=O)=C(O)[C@H](N(C)C)[C@H]3[C@H](O)[C@H]21]

In the context of the present invention, doxycycline also comprises the pharmaceutically acceptable salts thereof. The expression "pharmaceutically acceptable salt(s)" refers to the salts of a compound of interest that have the desired biological activity. The pharmaceutically acceptable salts comprise salts of acid or base groups present in the specified compounds. The pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc and diethanolamine salts. A list of pharmaceutically acceptable salts is notably published in the review by Berge et al. (J. Pharm. Sci. 1977, 66(1), 1-19).

The various pharmaceutically acceptable salts or the various forms of doxycycline used in the present invention are doxycycline hydrochloride, doxycycline monohydrate and doxycycline hyclate.

The presence of doxycycline as a second active agent in the compositions of the invention advantageously makes it possible, by the antibiotic properties thereof, to treat a rosacea associated with/exhibiting a resistance of *Demodex* to a compound of the avermectin family, particularly ivermectin. Indeed, a composition comprising ivermectin as the sole active agent is or can become ineffective for treating rosacea when *Demodex* becomes resistant to ivermectin. The combination with doxycycline is thus advantageous for delaying the onset of resistance or to act against resistant *Demodex*.

A particular object of the invention thus relates to a composition comprising a compound of the avermectin family, preferentially ivermectin, and doxycycline or a pharmaceutically acceptable salt thereof, for use in the treatment and/or the delaying of the onset of the symptoms of a rosacea associated with/exhibiting a resistance of *Demodex*, particularly a resistance of *Demodex* to avermectins, preferentially to ivermectin.

Another particular object of the invention relates to doxycycline or a pharmaceutically acceptable salt thereof for a use in combination with ivermectin in the treatment and/or the delaying of the onset of the symptoms of a rosacea associated with/exhibiting a resistance of *Demodex*, particularly a resistance of *Demodex* to avermectins, preferentially to ivermectin.

By the expression "rosacea associated with/exhibiting a resistance of *Demodex* to avermectins" is meant a rosacea exhibiting *Demodex* resistant to treatment with avermectins. Thus, a treatment based on a compound of the avermectin family alone becomes less effective or ineffective following this resistance.

In an embodiment, the compound of the avermectin family present in the composition represents between 0.001% and 10%, preferentially between 0.001 and 5% and more preferably between 0.1 and 2% by weight, in relation to the total weight of the composition. Advantageously, the compound of the avermectin family represents between 0.5 and 1%, preferably 0.5 or 1%, and more preferentially 1% by weight, in relation to the total weight of the composition.

In an embodiment, the doxycycline or a pharmaceutically acceptable salt thereof present in the compositions of the invention represents between 0.0001 and 5%, preferentially between 0.001 and 3% by weight in relation to the total weight of the composition. When a composition comprises several of these compounds, the total concentration thereof is comprised in the abovementioned quantities.

Additives

The compositions of the invention can comprise a physiologically acceptable medium, i.e. a medium compatible with the skin, the mucous membranes and/or the skin appendages. The compositions of the invention can also comprise a pharmaceutically or cosmetically acceptable vehicle, i.e. a vehicle suitable for a use in contact with human cells, with no toxicity, intolerance, irritation, undue allergic response and the like, and proportioned in a reasonable risk/benefit ratio.

The compositions of the invention can further comprise any additive or adjuvant commonly used in the pharmaceutical, dermatological or cosmetics field, compatible with the compound of the avermectin family and the presence of doxycycline.

Mention may be made particularly of sequestrants, antioxidant chelators, sunscreens, preservatives, for example DL-alpha-tocopherol, charges, electrolytes, humectants, dyes, common inorganic or organic acids or bases, fragrances, essential oils, cosmetic active agents, moisturizers, vitamins, essential fatty acids, sphingolipids, self-tanning compounds such as DHA, agents that soothe and protect the skin such as allantoin, penetration agents, emulsifiers, gelling agents, thickeners, buffers, lipophilic excipients, disintegrants, soluble agents, compression agents or a mixture thereof. Of course, the person skilled in the art will take care to choose this or these optional further compounds, and/or the quantity thereof, in such a way that the advantageous properties of the composition according to the invention are not, or are not substantially, altered.

As preservatives, mention may be made by way of example of quaternary ammoniums such as benzalkonium chloride; phenoxyethanol; benzylic alcohol; diazolidinyl urea; parabens, such as methylparaben, propylparaben or butylparaben; benzoic acid and the sodium or potassium salts thereof such as sodium benzoate; sorbic acid and the sodium or potassium salts thereof such as potassium sorbate; mercury derivatives such as phenylmercury salts (acetate, borate or nitrate) or thiomersal; or mixtures thereof.

As humectants, mention may be made particularly of glycerin and sorbitol.

As chelators, mention may be made by way of example of ethylenediaminetetraacetic acid (EDTA), as well as the derivatives or salts thereof, dihydroxyethylglycine, citric acid, tartaric acid or mixtures thereof.

As penetration agents, mention may be made particularly of propylene glycol, dipropylene glycol, propylene glycol dipelargonate, lauroglycol and ethoxydiglycol.

As fats usable in the invention, nonrestrictive mention may be made of oils and in particular mineral oils (vaseline oil), oils of plant origin (avocado oil, soybean oil), oils of animal origin (lanolin), synthetic oils (perhydrosqualene), silicone oils (cyclomethicone) and fluorinated oils (perfluoropolyethers). Fatty alcohols such as cetyl alcohol, fatty acids, waxes and gums, particularly silicone gums, can also be used as fats.

As emulsifiers and co-emulsifiers usable in the invention, mention may be made for example of esters of fatty acid and polyethylene glycol such as PEG-100 stearate, PEG-50 stearate and PEG-40 stearate; esters of fatty acid and polyol such as glyceryl stearate, sorbitan tristearate and oxyethylene sorbitan stearates available under the trade names Tween 20 or Tween 60, for example; and mixtures thereof.

As gelling agents, by way of non-limiting examples, mention may be made of the polyacrylamide family such as the mixture sodium acryloyldimethyltaurate copolymer /isohexadecane / polysorbate 80 sold under the name SIMULGEL™ 600 by the company SEPPIC™, the mixture polyacrylamide / C13-14 isoparaffin /laureth-7 such as, for example, that sold under the name SEPIGEL™ 305 by the company SEPPIC™, the family of acrylic polymers coupled to hydrophobic chains such as PEG-150 / decyl / methylene bis(4-cyclohexylisocyanate) (SMDI) copolymer sold under the name ACULYN™ 44 Aculyn ™44(polycondensate comprising at least as elements, a polyethyleneglycol with 150 or 180 moles of ethylene oxide, decyl alcohol and methylene bis(4-cyclohexylisocyanate) (SMDI), at 35% by weight in a mixture of propyleneglycol (39%) and water (26%)), the modified starch family such as the modified potato starch sold under the name Structure SOLANACE™ or mixtures thereof.

The preferred gelling agents are derived from the polyacrylamide family such as SIMULGEL™ 600 or SEPIGEL™ 305 -or mixtures thereof.

The composition can comprise one or more thickeners, making it possible to obtain a suitable viscosity, selected from the group consisting of polysaccharides, cellulose derivatives and CARBOPOL® -type carboxyvinyl polymers. These polymers comprise, but are not limited to, CARBOPOL® 934P, CARBOPOL® 71G, CARBOPOL® 971P and CARBOPL® 974P.

The composition can comprise one or more thickeners selected from cellulose derivatives. The cellulose derivatives usable as thickeners include, but are not limited to, methylcellulose, ethylcellulose, ethylmethylcellulose, carboxymethylcellulose, sodium carboxymethylcellulose and hydroxyalkylcelluloses such as hydroxyethylcellulose, hydroxymethylcellulose, hydroxypropylcellulose and hydroxypropylmethylcellulose, and a combination thereof.

The composition can comprise one or more thickeners selected from polysaccharides. The polysaccharides usable as a thickener include, but are not limited to, xanthan gum, gum tragacanth, carrageenans such as λ-carrageenan, κ-carrageenan or τ-carrageenan, galactomannans such as carob seed flour, guar seed flour or tara seed flour, gellan gum, gum arabic, gum karaya, pectins, starch and derivatives thereof obtained by esterification or etherification, and tamarind, and a combination thereof.

The composition can also comprise, as thickeners, a mixture of one or more cellulose derivatives and one or more polysaccharides.

The composition according to the invention can further comprise at least one disintegrant such as sodium carboxymethyl starch, cross-linked sodium carboxymethylcellulose or cross-linked polyvinylpyrrolidone, and more advantageously cross-linked polyvinylpyrrolidone.

The composition according to the invention can further comprise at least one polyol (or sugar-alcohol)-type soluble agent. A polyol (or sugar-alcohol) is a hydrogenated form of sugar wherein the carbonyl group (i.e. aldehyde or ketone) has been reduced to a primary or secondary hydroxyl group. In particular, the soluble diluent agent is selected from the group consisting of mannitol, xylitol, sorbitol, maltitol and a mixture thereof.

Said soluble agent is used in the forms of granules, powders or a mixture of granules and powders.

The composition of the invention can comprise compression agents for the technical production of tablets such as:
lubricants such as magnesium stearate, stearic acid, glycerol monostearate, polyoxyethyleneglycols having a molecular weight of 400 to 7,000,000, hydrogenated castor oil, glycerol behenate, mono-, bi- or tri-substituted glycerides, sodium stearyl fumarate;
flow agents, such as colloidal silica or any other silica, for example the product marketed by Degussa under the brand Aerosil;
binders such as starch, buffers, absorbents, diluents such as lactose as well as any other pharmaceutically acceptable additive.

These additives can be present in the composition in an amount of 0.0001 to 10% by weight in relation to the total weight of the composition. The concentration of these active agents and/or additives in the composition can vary according to nature of said additives and according to the envisaged mode of administration.

Application

The administration can be carried out by oral, topical, ocular, intraocular, intravenous, parenteral, subcutaneous, epicutaneous, intradermal, transdermal, intramuscular, enteral, rectal, intranasal, sublingual, buccal or intra-respiratory route or by nasal inhalation.

When the administration is carried out by topical route on the skin or by ocular route on the eye, the composition can be described as a dermatological composition.

Collyria are particularly suited to the ocular route. The composition administrable topically is more particularly intended for the treatment of the skin and the mucous membranes. By "topical application" is meant that the composition according to the invention is applied or spread on the surface of the skin or of a mucous membrane.

Among these routes of administration, the oral route, the topical route and the ocular route are particularly preferred and the oral route and the topical route are even more preferred.

For a topical application, compositions are envisaged in the form of solutions, lotions, gels, ointments, milk-type emulsions having a fluid or semi-fluid consistency obtained by dispersion of a fatty phase in an aqueous phase (O/W) or the reverse (W/O), or powders, saturated buffers, sprays, suspensions or emulsions having a soft, semi-fluid or solid consistency of the cream or ointment type, or microemulsions, microcapsules, microparticles or vesicular dispersions of the ionic and/or nonionic type. It can also appear in the form of microspheres or nanospheres or lipid or polymer vesicles or polymer patches and hydrogels allowing controlled release. These compositions are prepared according to the usual methods.

For a topical administration, the composition advantageously appears in the form of an ointment, cream, lotion or gel and a particularly suitable formulation is that proposed in the application WO 2004/093886.

A preferred topical composition of the invention is a composition comprising between 0.001 and 10% by weight of the compound of the avermectin family and between 0.0001 and 5% by weight of doxycycline or a pharmaceutically acceptable salt thereof in relation to the total weight of the composition. Preferably, the compound of the avermectin family represents between 0.001 and 5%, between 0.1 and 2%, between 0.5 and 1%, 0.5%, 1% and preferentially 1% by weight, in relation to the total weight of the composition. Preferably, doxycycline or a pharmaceutically acceptable salt thereof represents between 0.0001 and 5%, preferentially between 0.001 and 3% by weight, in relation to the total weight of the composition.

The compositions of the present invention can also appear in all the galenic forms normally used for oral administration, particularly in the form of tablets, capsules, pills, powder or any form for solid oral preparation or in any form of liquid oral preparation.

The pharmaceutical composition generally comprises a physiologically acceptable medium, for example for the preparation of tablets or capsules or for a liquid oral preparation such as the vehicles used entirely conventionally.

The composition according to the present invention can appear in the form of a traditional (monolayer) or multilayer tablet, in particular having 2 or 3 layers. When the pharmaceutical composition is for controlled release or prolonged release, the composition can be a multilayer tablet, one layer of which can have a specific disintegration time different from another layer. The composition can be also in the form of traditional capsules (containing powder) or of capsules comprising microgranules or of sachets comprising powder for a liquid oral preparation or granules.

The pharmaceutical compositions according to the present invention are of a size acceptable for traditional oral administration. Thus, compositions having a weight below 800 mg, preferably below 500 mg, and more particularly below 400 mg (such as for example compositions the weight of which is 150 mg, 200 mg or 250 mg) are preferred.

Advantageously, for oral administration, the composition comprises a tablet, capsule, pill or granules or is in powder form.

A preferred oral composition of the invention is a composition comprising between 0.001 and 10% by weight of the compound of the avermectin family and between 0.0001 and 5% by weight of doxycycline or a pharmaceutically acceptable salt thereof in relation to the total weight of the composition. Preferably, the compound of the avermectin family represents between 0.001 and 5%, between 0.1 and 2%, between 0.5 and 1%, 0.5%, 1% and preferentially 1% by weight, in relation to the total weight of the composition. Preferably, doxycycline or a pharmaceutically acceptable salt thereof represents between 0.0001 and 5%, preferentially between 0.001 and 3% by weight, in relation to the total weight of the composition.

In an embodiment, the term "treatment" or "to treat" refers to improvement, prophylaxis or reversal of a disease or a disorder, or at least one symptom that can be distinguished therefrom. In another embodiment, "treatment" or "to treat" refers to improvement, prophylaxis or reversal of at least one measurable physical parameter associated with the disease or disorder being treated, that is not necessarily discernible in or by the treated subject. In another further embodiment, "treatment" or "to treat" refers to inhibition or slowing of the progression of a disease or a disorder, physically, for example, stabilization of a discernible symptom, physiologically, for example, stabilization of a physical parameter, or both. In another embodiment, "treatment" or "to treat" refers to the delaying of the onset of a disease or disorder.

In certain embodiments, the compounds of interest are administered as a preventive measure. In the present context, this preventive measure refers to a reduction in the risk of acquiring a specified disease or disorder but also a reduction, an inhibition or a slowing of the onset of the symptoms related to this disease, namely rosacea. The symptoms characteristic of rosacea are for example erythemas, papules, pustules and telangiectasia.

Within the meaning of the present invention, by "patient" is meant any mammal, and more particularly human beings, men or women.

The quantity actually administered of the compound of the avermectin family and doxycycline or a pharmaceutically acceptable salt thereof and optionally other additives to be employed according to the invention depends on the therapeutic or cosmetic effect desired, and can thus vary to a great extent. The person skilled in the art, particularly the doctor, can easily, based on his general knowledge, determine the appropriate quantities. Thus, and according to a preferred embodiment, the pharmaceutical composition(s) is/are administered 1 to 2 times/day. Preferably, the treatment can have a duration of 1 week to 6 months, renewable, and preferably 2 weeks to 4 months. The treatments can be renewed in cycles with or without a rest period.

In the compositions according to the invention, the effective therapeutic dose of the compound of the avermectin family administered is 100 µg to 5 g, 100 µg to 3 g, 100 µg to 1 g, preferably 150 µg to 500 mg, and more preferentially 200 µg to 200 mg per day.

In the compositions according to the invention, the effective therapeutic dose of doxycycline or a pharmaceutically acceptable salt thereof administered is between 100 µg and 1 g, preferably between 100 µg and 500 mg, more preferentially between 10 and 300 mg per day, and still more preferably at an effective therapeutic dose of 40, 100 or 200 mg per day.

In the context of the invention, by "effective therapeutic dose" is meant the therapeutic dose that prevents, stops or reduces the deleterious effects of the rosacea treated in the patient. It is understood that the administered dose can be adapted by the person skilled in the art according to the patient, the type of rosacea, the mode of administration, etc.

Kits

Another object of the invention relates to a kit comprising (a) a composition comprising a compound of the avermectin family, preferentially ivermectin, and (b) a composition comprising doxycycline or a pharmaceutically acceptable salt thereof, as a combination product for simultaneous, separate or sequential use in the treatment and/or the delaying of the onset of the symptoms of rosacea.

Preferably, the kit according to the invention is used in the treatment and/or the delaying of the onset of the symptoms of subtype I, II and IV rosacea, advantageously subtype II rosacea.

Particularly, the kit according to the invention is used in the treatment and/or the delaying of the onset of the symptoms of a rosacea associated with/exhibiting a resistance of *Demodex*, particularly a resistance of *Demodex* to avermectins, preferentially to ivermectin.

The compositions of the kit can be packaged separately in separate containers which can appear in various forms. They can be particularly tubes or bottles. According to an embodiment, the two containers are independent of one another. According to a particular embodiment, the two compositions are packaged in a single device, said containers forming compartments joint to one another.

In a particular embodiment, the composition of the kit comprising a compound of the avermectin family is intended to be administered at an effective therapeutic dose of between 100 µg and 5 g, between 100 µg and 3 g, between 100 µg and 1 g, preferably between 150 µg and 500 mg, and more preferentially between 200 µg and 200 mg per day; and the composition comprising doxycycline or a pharmaceutically acceptable salt thereof is intended to be administered at an effective therapeutic dose of between 100 µg and 1 g, preferably between 100 µg and 500 mg, more preferentially between 10 and 300 mg per day, and still more preferably at an effective therapeutic dose of 40, 100 or 200 mg per day. The compound of the avermectin family and doxycycline or a pharmaceutically acceptable salt thereof are preferably administered by topical, oral or ocular route.

In a first embodiment, the compound of the avermectin family and doxycycline or a pharmaceutically acceptable salt thereof are administered by topical route.

In a second embodiment, the compound of the avermectin family and doxycycline or a pharmaceutically acceptable salt thereof are administered by oral route.

In a third embodiment, the compound of the avermectin family is administered by topical route and doxycycline or a pharmaceutically acceptable salt thereof is administered by oral route.

Another object of the invention relates to a composition as defined in the present application and comprising a compound of the avermectin family and doxycycline or a pharmaceutically acceptable salt thereof, for use in the treatment of demodicidosis, and more particularly demodicidosis associated with/exhibiting a resistance of *Demodex*, in particular a resistance of *Demodex* to avermectins, and preferentially to ivermectin. The present invention also relates to the use of a kit as disclosed in the present application for use in the treatment of demodicidosis, and more particularly demodicidosis associated with/exhibiting a resistance of *Demodex*, in particular a resistance of *Demodex* to avermectins, and preferentially to ivermectin.

The invention claimed is:

1. A method of improving or slowing progression of symptoms associated with rosacea exhibiting *Demodex* resistant to treatment with a compound of the avermectin family alone, the method comprising administering to an individual in need thereof an effective amount of a composition comprising the compound of the avermectin family with doxycycline or a pharmaceutically acceptable salt thereof.

2. The method according to claim 1, wherein the compound of the avermectin family is ivermectin.

3. The method according to claim 1, wherein the compound of the avermectin family represents 0.001% to 10% by weight of the total weight of the composition.

4. The method according to claim 3, wherein the compound of the avermectin family represents 0.5% to 1% by weight of the total weight of the composition.

5. The method according to claim 1, wherein the doxycycline or a pharmaceutically acceptable salt thereof represents 0.0001% to 5% by weight of the total weight of the composition.

6. The method according to claim 1, wherein the composition is formulated for topical or oral administration.

7. The method according to claim 1, wherein the compound of the avermectin family is administered at 100 µg to 5 g per day.

8. The method according to claim 1, wherein the doxycycline or a pharmaceutically acceptable salt thereof is administered at 100 µg to 1 g per day.

9. The method according to claim 3, wherein the compound of the avermectin family is present in an amount of 0.001% to 5% by weight of the total weight of the composition.

10. The method according to claim 3, wherein the compound of the avermectin family is present in an amount of 0.1% to 2% by weight of the total weight of the composition.

11. The method according to claim 4, wherein the compound of the avermectin family is present in an amount of 1% by weight of the total weight of the composition.

12. The method according to claim 5, wherein the doxycycline or salt thereof is present in an amount from 0.0001% to 3% by weight of the total weight of the composition.

13. The method according to claim 7, wherein the compound of the avermectin family is administered at 100 µg to 3 g per day.

14. The method according to claim 13, wherein the compound of the avermectin family is administered at 100 µg to 1 g per day.

15. The method according to claim 14, wherein the compound of the avermectin family is administered at 150 µg to 500 mg per day.

16. The method according to claim 15, wherein the compound of the avermectin family is administered at 200 µg to 200 mg per day.

17. The method according to claim 8, wherein the doxycycline or a pharmaceutically acceptable salt thereof is administered at 100 µg and 500 mg per day.

18. The method according to claim 17, wherein the doxycycline or a pharmaceutically acceptable salt thereof is administered at 10 µg and 300 mg per day.

19. The method according to claim 18, wherein the doxycycline or a pharmaceutically acceptable salt thereof is administered at 40 mg, 100 mg or 200 mg per day.

* * * * *